(12) United States Patent  
Foote (10) Patent No.: US 6,179,815 B1
(45) Date of Patent: Jan. 30, 2001

(54) LOW COMPLIANCE INFLATION/ DEFLATION SYSTEM

(75) Inventor: Jerrold Foote, Salt Lake City, UT (US)

(73) Assignee: Merit Medical Systems, Inc., South Jordan, UT (US)

( * ) Notice: Under 35 U.S.C. 154(b), the term of this patent shall be extended for 0 days.

(21) Appl. No.: 09/119,811

(22) Filed: Jul. 21, 1998

(51) Int. Cl.[7] ..................................................... A61M 5/00
(52) U.S. Cl. ...................... 604/181; 604/97.01; 604/236
(58) Field of Search ............................... 604/4, 181, 191, 604/97–100, 207, 236

(56) References Cited

U.S. PATENT DOCUMENTS

| | | | |
|---|---|---|---|
| 808,635 | * | 1/1906 | Ciolfi et al. . |
| 5,135,490 | * | 8/1992 | Strickland ............................... 604/50 |
| 5,476,450 | * | 12/1995 | Ruggio ................................... 604/93 |
| 5,584,803 | * | 12/1996 | Stevens et al. ........................... 604/4 |
| 5,755,686 | * | 5/1998 | O'Neill et al. .......................... 604/53 |
| 5,916,193 | * | 6/1999 | Stevens et al. ......................... 604/53 |

* cited by examiner

*Primary Examiner*—Wynn Wood Coggins
*Assistant Examiner*—Kevin C. Sirmons
(74) *Attorney, Agent, or Firm*—Workman Nydegger & Seeley (57) ABSTRACT

A system for selectively inflating and deflating a balloon of a dilation balloon catheter. The system includes an inflation syringe that generates a positive pressure for inflating the balloon and a vacuum source that generates a negative pressure for deflating the balloon. A valve is used to selectively establish fluid communication between the vacuum source and the catheter. The valve may be a manually operable device for alternatingly and selectively applying the positive and negative pressures to the catheter. Alternatively, the valve includes a port in a wall of the barrel of the inflation syringe. The port is obstructed when the plunger of the inflation syringe is advanced beyond a specified point in the barrel. An obstructed port isolates the negative pressure of the vacuum source from the catheter, while an opened port establishes fluid communication between the vacuum source and the catheter. The system may be used to position a stent in a treated artery of a patient. The stent is placed at the desired position using an inflated balloon, and the stent is released by deflating the balloon with the negative pressure.

16 Claims, 6 Drawing Sheets

LOW COMPLIANCE INFLATION/DEFLATION SYSTEM

BACKGROUND OF THE INVENTION

1. The Field of the Invention

The present invention relates to systems for applying inflation and deflation pressures to a catheter assembly. More particularly, the present invention relates to a system whereby a balloon of a dilation balloon catheter may be selectively and alternatingly inflated and deflated by the operation of an inflation syringe and a vacuum source, respectively.

2. Relevant Technology

In recent years, dilation balloon catheters have become increasingly useful in various medical procedures. For example, dilation balloon catheters have been used to reduce the intrusiveness of medical procedures in various fields of medicine, such as urology, gynecology, cardiology, and the like. Particularly in the treatment of coronary artery disease, the use of dilation balloon catheters and their associated fluid pressurization systems has become widespread.

Coronary artery disease is the narrowing of the arteries that feed oxygen-rich blood to the heart through the buildup of atherosclerotic plaque on the inner walls of the arteries. The heart needs adequate amounts of oxygen to continually and efficiently pump blood throughout the body. When arteries leading to the heart become narrowed and constricted due to coronary artery disease, several problems can develop. A person with coronary artery disease can experience angina, which is characterized by chest pain or pressure that radiates to the arm or jaw and is caused by a lack of oxygen-rich blood to the heart muscle. If untreated, coronary artery disease can lead to or contribute to heart failure and death.

In recent years, coronary angioplasty has become a common and accepted alternative to the vastly more intrusive coronary bypass surgery. Coronary bypass surgery involves surgical access to the heart, placing the patient on an extracorporeal blood oxygenation system so that the heart can be stopped for surgery, and then surgically attaching one or more passageways by which blood can bypass a clogged coronary artery, all under general anesthesia. Coronary angioplasty, which can be performed using a local anesthetic, involves running a dilation balloon catheter (a catheter having an inflatable balloon near the distal end) to a constricted region, or a stenosis, in the diseased artery and then inflating the balloon in order to radially compress atherosclerotic plaque within the artery, thereby obtaining increased blood flow to the heart. Compared to coronary bypass surgery, coronary angioplasty is less intrusive and traumatic, typically involves less risk to the patient, and significantly reduces the patient's discomfort and recovery time.

Dilation balloons are typically inflated using a pressure-generating device that forces pressurized inflation fluid through the lumen of the catheter to the balloon. Examples of pressure-generating devices include syringes and devices having an inflation wire slidably disposed in a lumen of the catheter. The inflation pressure and the duration of inflation of the dilation balloon are often monitored and displayed using appropriate electronic or mechanical sensors and display units so that the operating physician may conduct the coronary angioplasty procedure at the desired intensity and duration.

In addition to the feedback provided by the sensors that detect the pressure and duration of the inflation, some pressure-generating devices that include a relatively small-diameter inflation wire can give an experienced physician tactile feedback relating to the progress of the operation. The tactile feedback can relate to, for example, the progress of the plaque-compression procedure as the dilation balloon is inflated.

Conventional pressure-generating devices that allow tactile feedback suffer from several shortcomings. For example, such pressure-generating devices are conventionally integrally connected to a dilation balloon catheter. This prevents the pressure-generating devices from being interchangeably used with other catheter types. Additionally, the electronic sensors and display units are also integrally attached to such pressure-generating devices, with the result that the sensors and display units must be disposed after one use. Consequently, the cost of treatment using such pressure-generating devices includes the cost of relatively expensive sensors that are used only once. Using an inflation wire is also generally incompatible with the syringe model of inflating dilation balloons.

Pressure-generating devices that allow tactile feedback also have not been compatible with procedures involving the positioning of a stent, which is a support member such as a cylindrical wire coil, in a treated artery at the site of an angioplasty procedure. In a majority of coronary angioplasty procedures, stents are disposed within the treated arteries to prevent the arteries from radially collapsing, which is a common side effect of coronary angioplasty in the absence of stents. A stent is ordinarily applied to a patient by placing the stent on a dilation balloon and advancing the balloon to the desired location. The balloon is inflated in order to compress and position the stent against the interior wall of the artery. The stent is released from the balloon by generating a negative, or deflation, pressure within the dilation balloon. Deflation of the balloon allows the balloon to be withdrawn, while leaving the stent in the desired position within the patient. However, conventional pressure-generating devices that provide tactile feedback have not been capable of generating the negative pressure needed to be compatible with stent placement.

In view of the foregoing, there exists a need in the art for improved pressure-generating devices that can adequately inflate and deflate dilation balloons. There is also a need in the art for pressure-generating devices that provide tactile feedback to the operating physician while being compatible with stent placement procedures.

SUMMARY OF THE INVENTION

The present invention relates to systems for selectively and alternatingly inflating and deflating a balloon of a dilation balloon catheter by the operation of an inflation syringe and a vacuum source, respectively. The inflation syringe has a barrel and a plunger, with the distal end of the barrel being connected in fluid communication with the dilation balloon catheter. The barrel of the inflation syringe preferably has a diameter that is small enough to provide a desired degree of tactile feedback to the operating position as the physician inflates the balloon.

The balloon of the dilation balloon catheter is capable of being deflated by the vacuum source. The vacuum source is coupled to the catheter in such a manner that the physician can select and alternate between the vacuum source and the inflation syringe depending on the stage of the medical procedure. For example, if the dilation balloon is being used to place a stent within a treated artery, a positive pressure is applied to the dilation balloon using the inflation syringe, thereby securing the stent on the balloon. When the stent is positioned at the desired location within the treated artery, the physician places the vacuum source in fluid communication with the catheter and activates the vacuum source, thereby deflating the balloon and detaching the stent from the balloon. The catheter may then be retracted from the artery, with the stent remaining in position within the patient.

According to one embodiment of the invention, selection between negative pressure of the vacuum source and the positive pressure of the inflation syringe is accomplished using a manually operable valve. The vacuum source may be a vacuum syringe, which is connected to the catheter by means of the valve. In this case, the negative pressure may be generated by closing the valve and retracting and locking in place the plunger of the vacuum syringe. In order to apply the negative pressure to the balloon, the valve may be opened so that the vacuum syringe is placed in fluid communication with the catheter. In order to again generate and apply positive inflation pressure, the valve may be closed while the plunger of the inflation syringe is advanced within the barrel of the inflation syringe.

In another embodiment of the invention, the manually operable valve is replaced with a port formed in the wall of the barrel of the inflation syringe. The port is positioned on the inflation syringe so as to be selectively obstructed by the inflation syringe plunger. When the plunger is advanced within the barrel of the inflation syringe to a point where it obstructs the port, the negative pressure from the vacuum source is isolated from the catheter. When the vacuum pressure is needed, the physician retracts the inflation syringe plunger to a point where the opening is no longer obstructed, thereby exposing the vacuum source to the catheter and deflating the balloon.

The system may also be provided with a noncompliant, inflation fluid reservoir, in which excess inflation fluid is stored. The excess inflation fluid in the reservoir is provided to replace the inflation fluid that is withdrawn into the vacuum source during each application of the negative pressure. The reservoir ensures that enough inflation fluid remains in the catheter after application of negative pressure from the vacuum source so that the balloon may be subsequently reinflated.

The pressure within the catheter may be monitored using a pressure transducer in communication with the inflation fluid. The pressure transducer allows the physician to monitor the progress of the medical procedure in which the inflation and deflation system is used. Moreover, a luer fitting may be used to removably attach the inflation syringe and the vacuum source to the catheter.

In view of the foregoing, the inflation/deflation systems of the invention allow a dilation balloon to be selectively and alternatingly inflated and deflated and are thus compatible with stent placement procedures. Furthermore, the inflation syringes of the invention may be sized so as to provide tactile feedback to the operating physician, thereby allowing the physician to monitor the progress of the medical procedure.

These and other objects, features, and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The present invention relates to inflation and deflation systems for use with dilation balloon catheters wherein a positive pressure and a negative pressure may be selectively and alternatingly applied to the balloon catheter. The system includes an inflation syringe having a barrel diameter preferably small enough to provide a desired level of tactile feedback to the operating physician. As a plunger is advanced into the barrel of the inflation syringe, an inflation pressure is generated and directed to the dilation balloon catheter.

The inflation and deflation system further includes a vacuum source or another deflation device capable of reducing the pressure within the dilation balloon catheter to the extent that the balloon is deflated. The vacuum source may comprise a vacuum syringe selectively coupled with the dilation balloon catheter. The system further includes a valve positioned so as to selectively engage and disengage the vacuum source with the inflation fluid of the dilation balloon catheter. Using the valve, an operating physician may alternatingly apply the inflation pressure generated by the inflation syringe and the deflation pressure generated by the vacuum source, according to the stage of the medical procedure.

Figure 1:
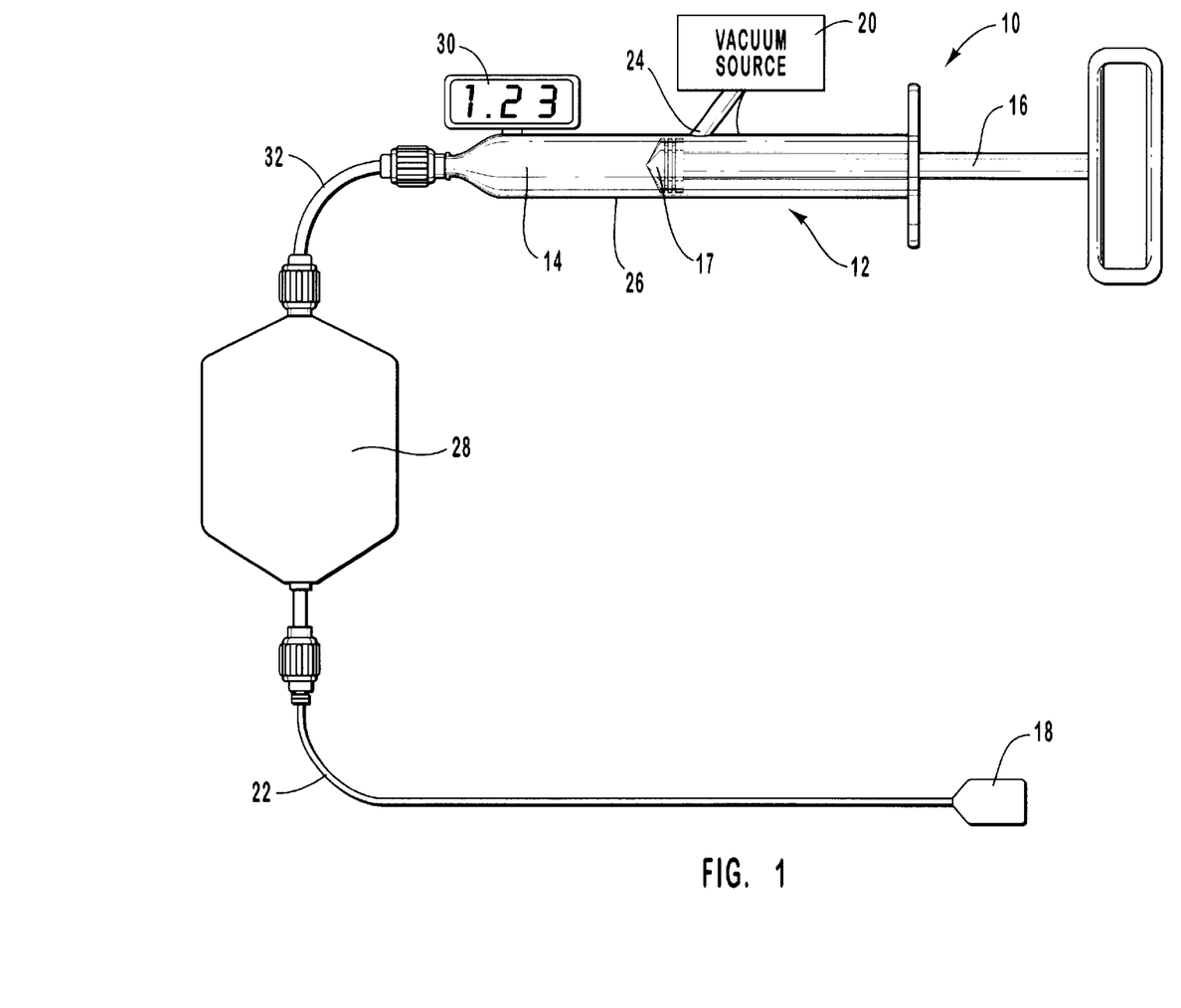
FIG. 1 is diagrammatic view of an inflation and deflation system of the invention coupled with a balloon dilation catheter.

FIG. 1 illustrates one embodiment of the inflation and deflation system of the invention. Inflation and deflation system 10 includes an inflation syringe 12 having a barrel 14 and a plunger 16. A plug 17 positioned at the distal end of plunger 16 sealingly engages the sidewall of barrel 14 as the plunger is advanced and retracted through the barrel. As plunger 16 is advanced through barrel 14, fluid is expelled through opening 19 at the distal end of inflation syringe 12. Because dilation balloon catheter 22 and inflation syringe 12 constitute a generally closed fluid system, a positive, elevated pressure is generated in the inflation fluid as plunger 16 is advanced through barrel 14. The positive pressure of the inflation fluid and the expulsion of the inflation fluid from inflation syringe 12 into dilation balloon catheter 22 combine to inflate or increase the volume of balloon 18 at the distal end of the catheter. Thus, inflation syringe 12 is but one example of syringe means for generating a positive fluid pressure sufficient to inflate a balloon of a dilation balloon catheter.

A typical plunger, such as plunger 16 of inflation syringe 12, has a plug 17 at its distal end and a gripping structure 21 at its proximal end. The gripping structure 21 or another similar extension of plunger 16 may be provided to allow a physician to grasp, manipulate, and advance or retract the plunger. As used herein, "advance", as used to describe the motion of a plunger with respect to a barrel, refers to motion of the plunger in the distal direction. "Retract", as used herein, refers to motion of the plunger in the proximal direction with respect to the barrel.

As used herein, the terms "positive pressure" and "positive fluid pressure" shall refer to fluid pressures greater than the pressure of the environment outside the inflation and deflation systems of the invention. Generally, a positive pressure is one that tends to increase the volume of a dilation balloon from an equilibrium state. The terms "negative pressure", "negative fluid pressure" and "vacuum pressure", as used herein, shall refer to fluid pressures less than the pressure of the environment outside the inflation and deflation systems of the invention. A negative pressure, when applied to a dilation balloon that is at least partially inflated, generally tends to decrease the volume of the dilation balloon. The term "fluid communication" as used herein is intended to mean that two or more portions or components of a fluid system are positioned relative to one another such that a fluid pressure is transmitted between and experienced by each of the two components. For example, when an inflation syringe and a dilation balloon are in fluid communication, each experiences substantially the same fluid pressure. In contrast, "fluid isolation" of one component with respect to another indicates that the components are not in fluid communication.

In one embodiment, barrel 14 preferably has a diameter that is small enough to provide a desired degree of tactile feedback to an operating physician during the use of inflation syringe 12 in a medical procedure. Tactile feedback may be provided to an operating physician by means of forces acting on plunger 16 and the relative ease of moving of plunger 16 during a medical procedure. For example, as a physician advances plunger 16 into barrel 14, the action of the plunger can communicate information to the physician relating to the ongoing inflation of balloon 18. If the inflation of balloon 18 is somehow inhibited by conditions within the patient's cardiovascular system, the physician may sense a corresponding reaction of plunger 16 as it is advanced into barrel 14. Likewise, the reaction of plunger 16 may indicate to the physician that balloon 18 has successfully compressed plaque in a diseased artery.

It is noted that the amount of fluid displaced by an inflation syringe as a plunger is advanced through a given distance into a barrel is inversely proportional to the cross sectional area of the barrel. For example, if the cross sectional area of barrel 14 were decreased by 50%, plunger 16 would need to be advanced about twice as far into the barrel in order to generate the same amount of inflation in the balloon 18.

Since the distance through which a plunger must be advanced into a barrel in order to produce a given amount of balloon inflation is inversely proportional to the cross sectional area of the barrel, the intensity of tactile feedback increases as the barrel diameter decreases. According to this principle, the degree of tactile feedback is negligible for inflation syringes that are larger than a threshold diameter. According to one embodiment of the invention, the diameter of barrel 14 of inflation syringe 12 is preferably small enough to communicate a desired degree of tactile feedback to the physician. Of course, tactile feedback is also related to the medical procedure in which the system is used. However, it has been found that a barrel diameter less than about 2 millimeters may be used in many dilation balloon catheter procedures to provide an adequate degree of tactile feedback. It is noted that the invention is not limited to inflation syringes of the foregoing specified diameter. Optionally, the diameter of the inflation syringes of the inflation and deflation systems of the invention may be selected without regard to tactile feedback considerations.

Inflation and deflation system 10 further includes a vacuum source 20 such as a vacuum syringe or another structure or device for generating deflation pressure. Preferably, vacuum source 20 may be connected with catheter 22 according to valve means for selectively establishing fluid communication between the vacuum source and the dilation balloon catheter. One example of the valve means is a port 24 formed in sidewall 26 of inflation syringe 12. Port 24 is preferably positioned on syringe 12 at a location so as to be obstructed by plunger 16 when the plunger is advanced beyond a specified point in barrel 14. When plunger 16 obstructs port 24, vacuum source 20 is isolated from catheter 22. However, when plunger 16 is subsequently retracted a sufficient distance through barrel 14, port 24 is exposed so as to establish fluid communication between vacuum source 20 and catheter 22. Accordingly, the valve means permits a physician to selectively and altentingly apply inflation pressure using syringe 12 and deflation pressure using vacuum source 20 as desired during the course of a medical procedure.

It can be appreciated that each time vacuum source 20 is placed in fluid communication with catheter 22, a quantity of inflation fluid generally flows into vacuum source 20. Thus, the inflation and deflation system 10 also preferably includes reservoir means for providing a supply of inflation fluid to the dilation balloon catheter sufficient to substantially compensate for any inflation fluid withdrawn from the catheter during operation of the vacuum source. One example of such reservoir means is an inflation fluid reservoir 28 that is substantially noncompliant and nondistensible. Inflation reservoir 28, when present, stores excess inflation fluid that is made available to catheter 22 and syringe 12 during repeated inflation cycles. Inflation fluid reservoir 28 is preferably noncompliant and nondistensible to the extent that actuation of inflation syringe 12 causes inflation of balloon 18 substantially without also causing inflation of reservoir 28. Alternatively, other structures that may be used to repeatedly supply adequate inflation fluid to catheter 22 and inflation syringe 12 may constitute the reservoir means.

According to an embodiment of the invention, the inflation and deflation system 10 further includes pressure monitoring means for detecting and displaying a magnitude of the fluid pressure generated by inflation syringe 12. One example of such pressure monitoring means is a pressure monitoring device 30, which preferably includes a sensor surface placed in fluid communication with syringe 12. Such fluid communication may be established by mounting pressure monitoring device 30 directly on syringe 12, on pressure tubing 32 extending from syringe 12, or according to any other arrangement whereby pressure monitoring device 30 may sense the pressure within the syringe 12. Any suitable pressure transducer or pressure gauge may be used, including those conventionally utilized in monitoring pressure generated by inflation syringes. Moreover, the pressure monitoring means may include a mechanical sensor, a piezoresistive semiconductor transducer, or any other suitable sensor for detecting the magnitude of the fluid pressure.

Figure 2A:
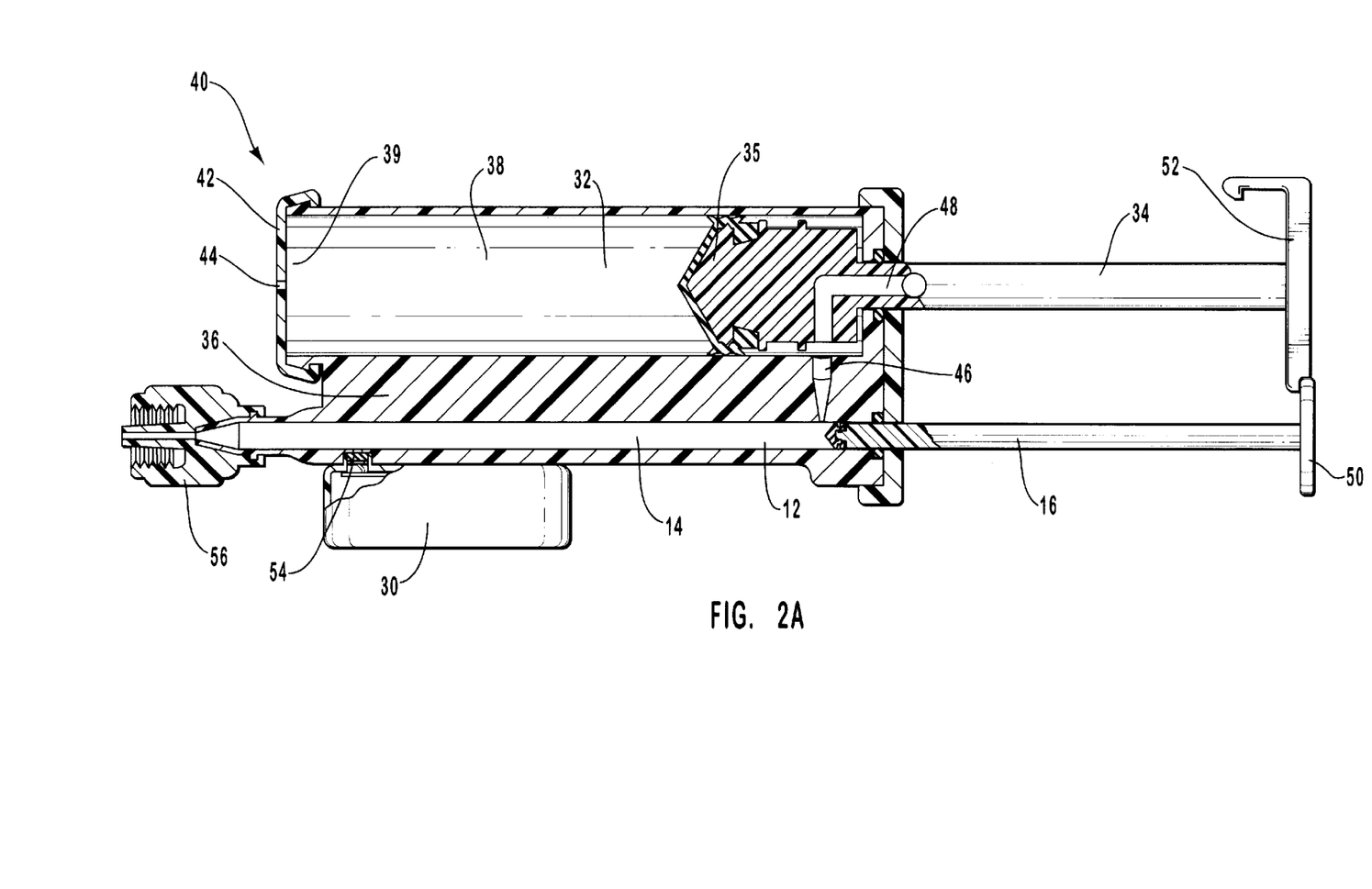
FIGS. 2A–2C are cross sectional elevation views illustrating one embodiment of the invention having an inflation syringe and a vacuum syringe in various stages of deployment.
Figure 2B:
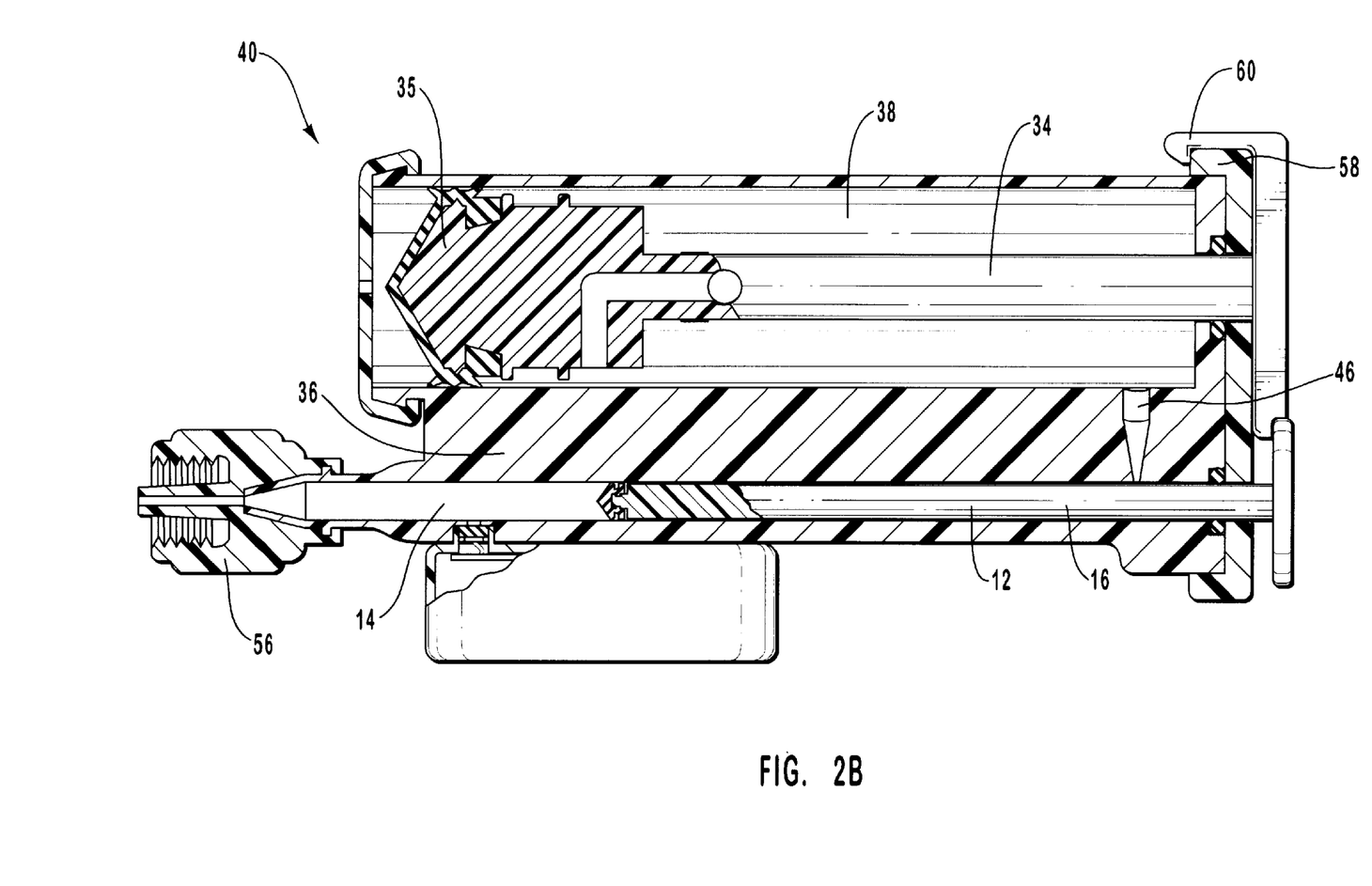
Figure 2C:
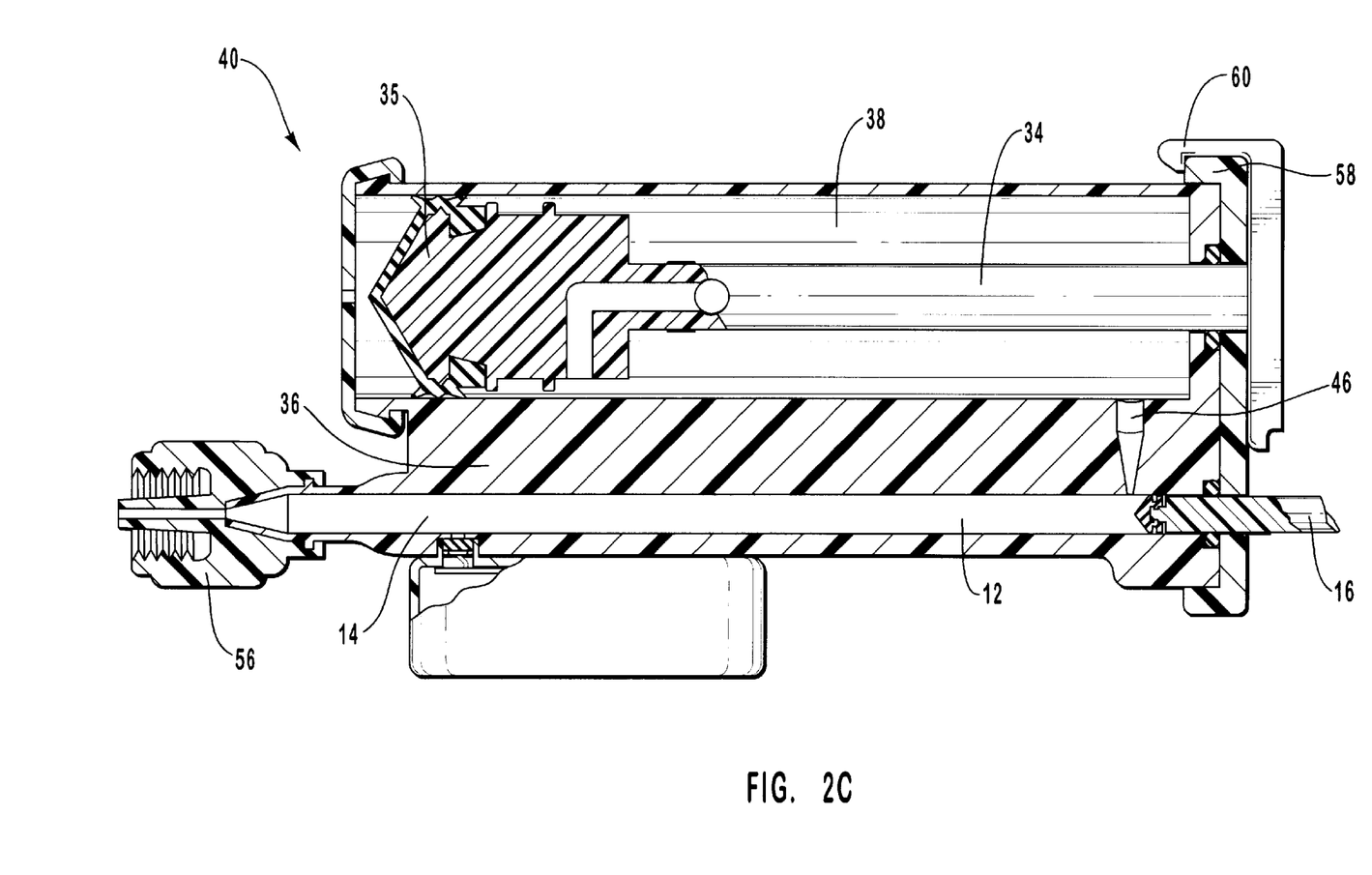

FIGS. 2A–2C depict another embodiment of the inflation and deflation system of the invention. By way of overview, FIG. 2A illustrates an inflation syringe 12 and a vacuum syringe 32 in a preliminary stage of a medical procedure, wherein no significant positive pressure has been generated with the inflation syringe and no significant negative pressure has been generated with the vacuum syringe. In FIG. 2B, the plungers 16, 34 of the inflation syringe 12 and the vacuum syringe 32, respectively, have been fully advanced. Accordingly, inflation syringe 12 has generated a positive pressure that may be used to inflate a dilation balloon, for example. Furthermore, a negative pressure is stored in vacuum syringe 32 and remains isolated from any catheter that may be attached to the inflation and deflation system. In FIG. 2C, plunger 16 of inflation syringe 32 has been retracted to a point where the negative pressure of vacuum syringe may be applied to deflate the dilation balloon.

Turning now to FIG. 2A, inflation and deflation system 40 includes inflation syringe 12 and a vacuum syringe 32. According to this embodiment, inflation syringe 12 and vacuum syringe 32 are preferably integrally formed in a body 36 comprising a suitable, medical grade, rigid material. Inflation syringe 12 generates a positive pressure within barrel 14 as plunger 16 is advanced thereinto. In contrast, vacuum syringe 32 generates a negative pressure in barrel 38 as plunger 34 is advanced thereinto. Accordingly, vacuum syringe 32 is but one example of a vacuum means for generating a negative fluid pressure sufficient to deflate a balloon of a dilation balloon catheter. The other examples of vacuum sources and deflation syringes disclosed herein represent further structures that correspond to the vacuum means of the invention. The system as illustrated in FIG. 2A shows plunger 16 of inflation syringe 12 and plunger 34 of vacuum syringe 32 both fully retracted. The manner in which syringes 12 and 32 generate the fluid pressures is further described below in reference to FIGS. 2B and 2C.

As illustrated in FIG. 2A, barrel 38 has an end 39 covered by a diaphragm 42 having an aperture 44 formed therein. Diaphragm 42 may be formed, for example, from a resilient polymeric material and stretched over end 39. Alternatively, diaphragm 42 may be eliminated and end 39 may be substantially open to the environment. In any event, end 39 is preferably configured such that plunger 34 and plug 35 may be advanced through barrel 38 from the initial retracted position illustrated in FIG. 2A substantially without building up a positive pressure between plug 35 and end 39 with respect to the ambient air pressure.

Body 36, according to this embodiment of the invention, preferably includes a port 46 extending from barrel 14 to barrel 38, which functions as valve means in substantially the same manner as port 24 of FIG. 1. Moreover, when plungers 16 and 34 are in the fully retracted positions illustrated in FIG. 2A, port 46 may be aligned with a channel 48 extending through a portion of plunger 34. The alignment of port 46 and channel 48 as illustrated in FIG. 2A provides a passageway through which inflation fluid may be introduced into syringe 12 and any accompanying catheter that has been attached thereto.

Plunger 16 and plunger 34 may conveniently include mechanically interfering handle structures or flanges to coordinate the movement of the plungers. For example, plunger 16 may have a handle 50 extendig radially away from the remainder of plunger 16. Likewise, plunger 34 may have a flange 52 extending radially away from the remainder of plunger 34 so as to contact handle 50. According to one embodiment, the mechanical interference between handle 50 and flange 52 causes corresponding advancement of plunger 34 as the physician manually advances plunger 16. Likewise, the mechanical interference between handle 50 and flange 52 prevents plunger 34 from being retracted beyond the corresponding position of plunger 16. However, the invention may be practiced in the absence of mechanically interfering portions of plunger 16 and plunger 34.

Inflation and deflation system 40 further includes a pressure transducer 54 in a pressure monitoring device 30. By way of example and not limitation, a preferred pressure monitoring device 30 is available from Merit Medical Systems, Inc. of South Jordan, Utah under the trade name Monarch.

Inflation and deflation system 40 may advantageously include connection means for releasably connecting the inflation and deflation system to a catheter. One suitable example of the connection means is luer coupler 56. In this example, the catheter would have a corresponding luer coupler that may be used to releasably engage coupler 56. The luer couplers used with the invention may be any suitable devices conventionally used in connecting tubing in medical environments.

FIG. 2B illustrates inflation and deflation system 40 wherein plungers 16 and 34 have been fully advanced into their respective barrels 14 and 38. During the advancement of plunger 16, port 46 is obstructed by the plunger, thereby removing vacuum syringe 32 from fluid communication with syringe 12. Advancement of plunger 16 generates positive inflation pressure within barrel 14 and within a catheter that may be attached thereto. Furthermore, advancement of plunger 34 generates negative pressure within barrel 38 and behind plug 35. The sealing engagement between plug 35 and barrel 38 substantially ensures that negative pressure within barrel 38 remains until it is accessed by the physician or until plunger 34 is retracted.

As seen in FIG. 2B, in one embodiment, a locking member 60 attached to plunger 34 mechanically engages a portion of body 36 so as to lock plunger 34 in a fixed position when it is fully advanced into barrel 38. For example, locking member may snap over resilient member 58 positioned at the proximal end of body 36. The interlocking relationship of locking structure 60 and body 36 prevents the ambient air pressure from causing plunger 34 to be prematurely retracted from barrel 38.

FIG. 2C illustrates the system during a deflation stage wherein a negative pressure within barrel 38 is placed in fluid communication with syringe 12 and the catheter that may be attached thereto. During this stage of the procedure, plunger 16 is retracted from barrel 14 to a point where port 46 is no longer obstructed, thereby establishing an open passageway from barrel 38 into barrel 14. When the negative pressure from vacuum syringe 32 has been applied through port 46 as desired, the physician may advance plunger 16 into barrel 14 so as to again isolate vacuum syringe 32 from the remainder of the fluid system. Furthermore, a positive inflation pressure may again be generated using syringe 12 by sufficiently advancing plunger 16.

Figure 3:
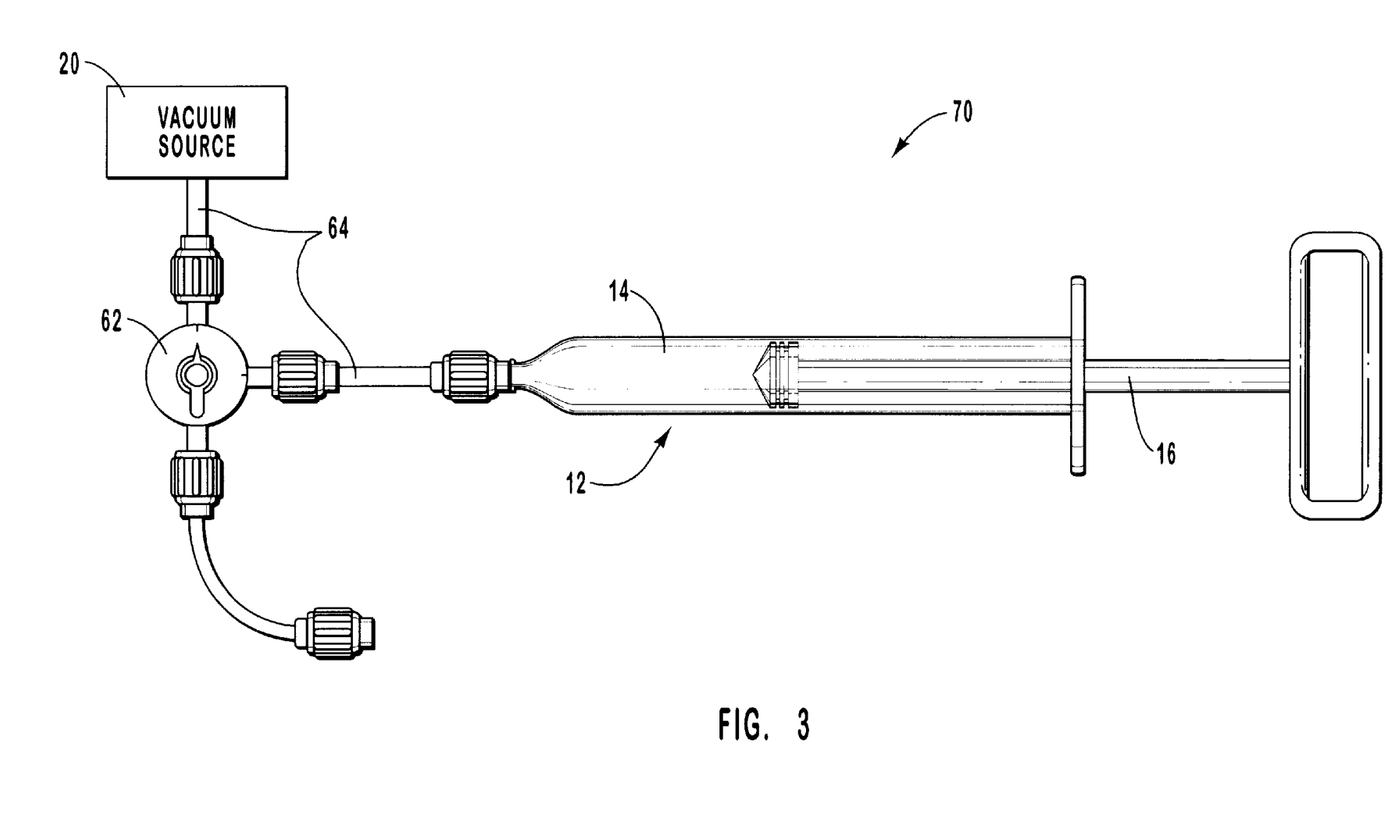
FIG. 3 is a diagrammatic view of an alternative embodiment of an inflation and deflation system according to the invention.

FIG. 3 illustrates yet a further embodiment of the inflation and deflation system of the invention. In particular, inflation and deflation system 70 includes a manually operable valve 62, which is another example of the valve means of the invention. The manually operable valve 62 allows a physician to selectively apply a negative pressure using vacuum source 20 or a positive pressure using inflation syringe 12. As seen in FIG. 3, the manually operable valve 62 may be attached to segments of pressure tubing 64 extending from both of inflation syringe 12 and vacuum source 20. When valve 62 is in a first position, the valve provides an open passageway between vacuum source 20 and the catheter, while isolating inflation syringe 12. Rotation of valve 62 into a second position establishes an open passageway from inflation syringe 12 to the catheter, and isolates vacuum source 20. The vacuum source 20 may be similar to those used in inflation and deflation systems 10 and 40.

Figure 4A:
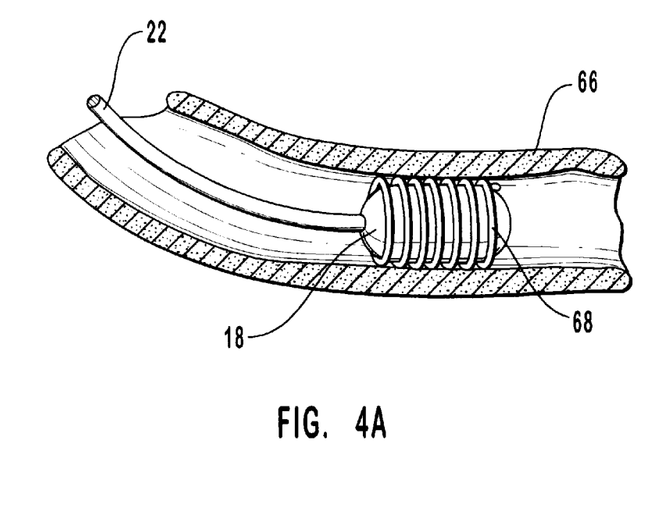
FIGS. 4A and 4B are partial views of a dilation balloon catheter being employed in a stent placement procedure.
Figure 4B:
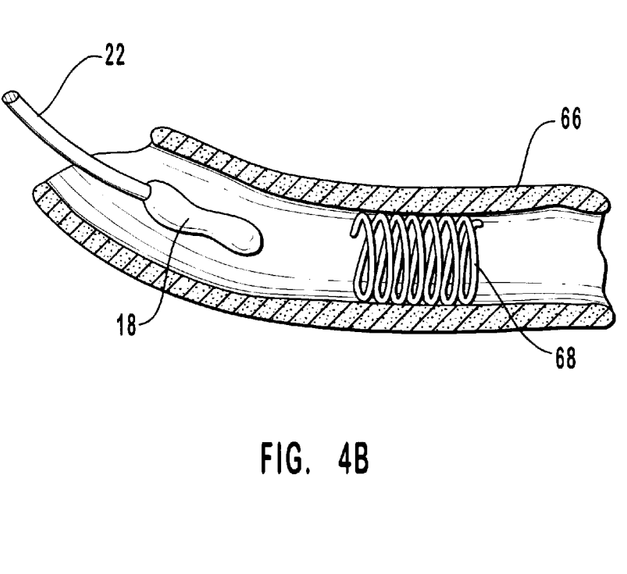

The inflation and deflation systems disclosed herein may be used in combination with a dilation balloon catheter in a process of positioning a stent within the cardiovascular system of a patient as illustrated in FIGS. 4A and 4B. The inflation and deflation of balloon 18 may be performed by alternatingly applying inflation and deflation pressures using the structures disclosed herein. For example, after a diseased artery 66 has been treated in a coronary angioplasty procedure, a stent 68, which is generally a helically wound wire or the like, is positioned at the site of treatment in order to prevent the diseased artery from collapsing. In a first step of the stent placement procedure, stent 68 is disposed on balloon 18 while the balloon is inflated. Inflation may be conducted using the structures disclosed herein for providing a positive inflation pressure. The force exerted by the inflated balloon 18 on stent 68 securely holds the stent in position on the balloon. The balloon 18 and stent 68 are then advanced through the diseased artery 66 to the desired position. Once stent 68 is in position, balloon 18 may be further inflated in order to slightly expand the stent.

Next, as illustrated in FIG. 4B, balloon 18 is deflated by selectively applying negative pressure to catheter 22 using the structures disclosed herein. Deflated balloon 18 is decoupled from stent 68, which remains in its selected position within diseased artery 66. Catheter 22 and deflated balloon 18 may then be retracted from stent 68.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for use in inflating and deflating a balloon of a dilation balloon catheter, said apparatus comprising:
   syringe means for advancing a plunger through a barrel in order to generate a positive fluid pressure sufficient to inflate a balloon of dilation balloon catheter;
   vacuum means for generating a negative fluid pressure sufficient to deflate said balloon when fluid communication is established between said vacuum means and said dilation balloon catheter; and
   valve means for selectively establishing said fluid communication between said vacuum means and said dilation balloon catheter, said valve means comprising a port extending from said vacuum means to a barrel of said syringe means, wherein said port may be selectively obstructed by positioning a plunger of said syringe means over said port, and wherein said port may be selectively opened by withdrawing said plunger from said port.

2. An apparatus as defined in claim 1, wherein said syringe has an inner diameter less than or equal to about 2 millimeters.

3. An apparatus as defined in claim 1, further comprising reservoir means for providing a supply of inflation fluid to said dilation balloon catheter and said syringe means sufficient to substantially compensate for any inflation fluid withdrawn from said fluid system and said syringe means during operation of said vacuum means.

4. An apparatus as defined in claim 3, wherein said reservoir means comprises a chamber having substantially non-distensible walls.

5. An apparatus as defined in claim 1, further comprising pressure monitoring means for detecting and displaying a magnitude of said positive fluid pressure generated by said syringe means.

6. An apparatus as defined in claim 1, wherein said vacuum means comprises a vacuum syringe including a barrel and a plunger, wherein said plunger may be actuated to generate said negative pressure within said barrel.

7. An apparatus as defined in claim 1, further comprising connection means for releasably connecting said apparatus to said dilation balloon catheter.

8. An apparatus as defined in claim 1, wherein said valve means comprises a manually operable valve that may be selectively actuated to establish fluid communication between said vacuum means and said dilation balloon catheter.

9. An apparatus for inflating and deflating a balloon of a dilation balloon catheter, said apparatus comprising:
   a first syringe having a first plunger disposed in a first barrel such that said first syringe generates a positive fluid pressure in a dilation balloon catheter as said first plunger is advanced into said first barrel;
   a second syringe having a second plunger disposed in a second barrel such that said second syringe generates a negative fluid pressure in said dilation balloon catheter when said second plunger is located at a selected position within said second barrel and said second syringe is in fluid communication with said dilation balloon catheter;
   a valve for selectively establishing said fluid communication between said second syringe and said dilation balloon catheter, said valve comprising a port extending from said first barrel to said second barrel, said port being obstructed when said first plunger is inserted into the first barrel up to a first position within said first barrel and said port being open when said plunger is retracted out of the first barrel to a second position within said first barrel; and
   a reservoir containing a supply of inflation fluid to substantially compensate for a quantity of inflation fluid that is removed by said second syringe.

10. An apparatus as defined in claim 9, where said valve is manually operable so as to permit said positive fluid pressure and said negative fluid pressure to be alternatingly and mutually exclusively applied to said dilation balloon catheter.

11. An apparatus defined in claim 9, further comprising a luer fitting for releasably connecting said dilation balloon catheter to said apparatus.

12. An apparatus for use in inflating and deflating a balloon of a dilation balloon catheter, said apparatus comprising:
   a dilation balloon catheter including a lumen and a balloon disposed at a distal end of said lumen;
   a first syringe for generating a positive pressure within said dilation balloon catheter, said first syringe including a first plunger selectively positionable within a first barrel;
   a second syringe for generating a negative pressure within said dilation balloon catheter when said second syringe is in fluid communication with said dilation balloon catheter, said second syringe including a second plunger selectively positionable within a second barrel;

a valve for selectively establishing said fluid communication between said second syringe and said dilation balloon catheter, said valve including a port extending from said first barrel to said second barrel, wherein said port is obstructed by said first plunger when said first plunger is inserted into the first barrel up to a first position within said first barrel and wherein said port is open when said first plunger is retracted out of the first barrel to a second position within said first barrel;

a reservoir containing a supply of inflation fluid to substantially compensate for a quantity of inflation fluid that is removed by said second syringe; and a pressure monitoring device for detecting and displaying a magnitude of said positive pressure.

13. An apparatus as defined in claim 12, further comprising a luer fitting for removably connecting said dilation balloon catheter to said first syringe.

14. An apparatus as defined in claim 12, further comprising a stent disposed on said balloon.

15. An apparatus as defined in claim 12, wherein each of said first plunger and said second plunger includes a mechanically interfering extension, whereby the distance that said second plunger may be retracted through said second barrel is limited according to the position of said first plunger in said first barrel.

16. An apparatus as defined in claim 15, wherein said second syringe is defined within a body, and wherein said second plunger comprises a locking member that engages said body when said second plunger is advanced to a selected position within said second barrel, said locking member sufficiently engaging said body so as to substantially prevent a pressure differential between the ambient pressure and said negative pressure within said second barrel from retracting said second plunger through said second barrel.

* * * * *

UNITED STATES PATENT AND TRADEMARK OFFICE
CERTIFICATE OF CORRECTION

PATENT NO. : 6,179,815 B1
DATED : January 30, 2001
INVENTOR(S) : Jerrold Foote

It is certified that error appears in the above-identified patent and that said Letters Patent is hereby corrected as shown below:

Column 3,
Line 53, before "inflated" change "altematingly" to -- alternatingly --

Column 4,
Line 29, after "and" change "altematingly" to -- alternatingly --
Lines 44-45, after "may" change "alt-entingly" to -- alt-ernatingly --

Column 6,
Line 26, after "and" change "altentingly" to -- alternatingly --.

Column 9,
Line 13, before "applying" change "altematingly" to -- alternatingly --

Column 10,
Line 43, after "said" and before "plunger" insert -- first --
Line 51, after "to be" change "altematingly" to -- alternatingly --

Signed and Sealed this

Twenty-sixth Day of February, 2002

Attest:

JAMES E. ROGAN
*Attesting Officer*     *Director of the United States Patent and Trademark Office*